United States Patent [19]
Migliori et al.

[11] Patent Number: 5,351,543
[45] Date of Patent: Oct. 4, 1994

[54] CRACK DETECTION USING RESONANT ULTRASOUND SPECTROSCOPY

[75] Inventors: Albert Migliori; Thomas M. Bell, both of Santa Fe; George W. Rhodes, Albuquerque, all of N. Mex.

[73] Assignee: The Regents of the University of California, Office of Technology Transfer, Alameda, Calif.

[21] Appl. No.: 813,651

[22] Filed: Dec. 27, 1991

[51] Int. Cl.$^5$ ............................................. G01N 29/12
[52] U.S. Cl. ........................................ 73/579; 73/659
[58] Field of Search ................. 73/579, 598, 602, 582, 73/659

[56] References Cited

U.S. PATENT DOCUMENTS

| | | | |
|---|---|---|---|
| 2,915,897 | 12/1959 | Hoffmann | 73/579 |
| 3,634,759 | 1/1972 | Koshikawa | 73/579 |
| 4,428,235 | 1/1984 | Sugiyama | 73/579 |
| 5,062,296 | 11/1991 | Migliori | 73/579 |
| 5,144,838 | 9/1992 | Tsuboi | 73/579 |
| 5,258,923 | 11/1993 | Imam et al. | 73/579 |

*Primary Examiner*—Hezron E. Williams
*Assistant Examiner*—Nashmiya Ashraf
*Attorney, Agent, or Firm*—Ray G. Wilson

[57] ABSTRACT

Method and apparatus are provided for detecting crack-like flaws in components. A plurality of exciting frequencies are generated and applied to a component in a dry condition to obtain a first ultrasonic spectrum of the component. The component is then wet with a selected liquid to penetrate any crack-like flaws in the component. The plurality of exciting frequencies are again applied to the component and a second ultrasonic spectrum of the component is obtained. The wet and dry ultrasonic spectra are then analyzed to determine the second harmonic components in each of the ultrasonic resonance spectra and the second harmonic components are compared to ascertain the presence of crack-like flaws in the component.

10 Claims, 3 Drawing Sheets

CRACK DETECTION USING RESONANT ULTRASOUND SPECTROSCOPY

This invention is in part the result of a contract with the Department of Energy (Contract No. W-7405-ENG-36).

BACKGROUND OF THE INVENTION

This invention relates to ultrasonic inspection and, more particularly, to ultrasonic resonance spectroscopy for detecting crack-like defects.

Sound waves, i.e. ultrasonics, are used to perform a variety of nondestructive measurements for quality control in manufacturing processes and in detecting flaws and component characteristic changes arising from use of a component. One well known process uses echoes to locate crack-like defects at or below surfaces, as well as internal cavities and flaws. Such processes require sensitive equipment for echo detection and experienced operators to interpret the echo results.

Yet another ultrasonic inspection technique uses ultrasonic resonance characteristics to provide information on features of a specimen. For example, U.S. Pat. No. 4,428,235, issued Jan. 31, 1984, teaches a method for flaw characterization by comparing an ultrasonic resonance spectrum determined experimentally with a pattern obtained from a specimen being investigated. Four characteristic parameters are analyzed, namely (1) maximum spectrum strength, (2) center frequency, (3) mean value of frequency spacing between maxima in a frequency spectrum, and (4) standard deviation of the frequency spacing. These characteristics are used to determine changes in attributes of the specimen being examined. However, this technique requires that baseline or other reference information be known.

U.S. Pat. No. 4,829,823, issued May 16, 1989, describes a defect detection system using ultrasonic resonances. A mathematical model is established using known resonance frequencies of one or more exemplary work pieces having acceptable known characteristics, e.g., the coefficients of elasticity, weight, localized defects, and the like. The resonance frequencies for subsequent work pieces are then measured around frequency locations corresponding to the resonance frequencies of the exemplary pieces. Using the mathematical model, the selected characteristics of the subsequent work piece can be calculated from shifts in the resonance frequencies and used as a measure of acceptance or rejection of the piece. Again, exemplary measurements are required in order to implement the ultrasonic inspection scheme.

The need for exemplary data is overcome by the present invention and crack detection is accomplished by ultrasonic resonance inspection of a completed work piece without the need for a known standard or "good" resonance pattern. Accordingly, it is an object of the present invention to provide ultrasonic flaw detection from resonance characteristics of a single object.

It is another object of the present invention to enable the detection of incipient flaws in a work piece without the need for comparative resonance spectrum data.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, this invention may comprise a method for detecting crack-like flaws in a component using resonance ultrasound spectroscopy. The component is first established in a first condition to produce a first response of the crack-like flaw to acoustic excitation. The component is then acoustically excited over a selected range of resonant ultrasound frequencies to generate a first spectrum of second harmonic components in the response to acoustic excitation relative to the first condition. The component is then placed in a second condition to produce a second response of the crack-like flaw to acoustic excitation. Using the selected range of resonant ultrasound frequencies, the component is again acoustically excited to generate a second spectrum of second harmonic components in the response of the component. The first and second spectra are compared to determine the presence of any crack-like flaws.

In a particular embodiment of the present invention, a first ultrasonic resonance spectrum of a component is generated using a plurality of exciting frequencies with the component in a dry condition. The component is then wetted with a selected liquid effective to penetrate crack-like flaws and a second ultrasonic resonance spectrum of the component is generated from the plurality of exciting frequencies. Second harmonic frequency components in the first and second ultrasonic resonance spectra related to each one of the plurality of exciting frequencies are then determined and compared to ascertain the presence of crack-like flaws in the component.

In another characterization of the present invention, apparatus is provided for detecting crack-like flaws in an object using the ultrasonic resonance spectrum. Oscillator means generates from a plurality of exciting frequencies an ultrasonic resonance spectrum of an object. Heterodyne means then generates a second harmonic spectrum from the resonance spectrum where each second harmonic component is related to each one of the plurality of exciting frequencies. Recording means then records successive ones of the second harmonic spectrum to enable crack-like flaws in the object to be detected.

BRIEF DESCRIPTION OF THE DRAWINGS

The accompanying drawings, which are incorporated in and form a part of the specification, illustrate an embodiment of the present invention and, together with the description, serve to explain the principles of the invention. In the drawings.

DETAILED DESCRIPTION

In accordance with the present invention, the presence of crack-like flaws in the surface of an object, e.g., stress and corrosion cracks, is determined by comparing the second harmonic components in the resonance response spectra from the component under at least two conditions that differently affect the second harmonic components of the response spectrum. This method can be used at any time in the life of an object and can be used with objects that have no prior resonant ultrasound spectrum.

Consider a solid object with a crack in the surface. The crack is essentially closed shut under conditions of no stress. When high-frequency ultrasound is applied to the object, pressure forces from the sound cause the crack to open and close slightly against air pressure. The resonance frequencies in this "dry" condition may be shifted from those obtained in an uncracked part, but no conclusions can be drawn about crack-like defects unless a reference spectrum is available.

If the object is now wetted with a liquid effective to penetrate crack-like flaws, such as a volatile solvent or a wax, the cracks fill with the liquid and stay filled. The "wet" object then will exhibit a significant difference in both the first and second harmonic components of the resonance response spectrum. One change is that the ultrasonic attenuation of the first harmonic may become significantly larger with liquid-filled cracks vs. air-filled cracks. Thus, the object with crack-like defects will show slightly broadened resonances after the liquid is introduced.

Another property of the cracks is that during application of ultrasound, for each half-cycle of sound that produces tensile stress, the crack opens. For each half-cycle of sound producing compressive stress the crack slams shut, or tries to. Thus, a part with cracks exhibits a different response for each half cycle. If the cracks are filled with air, a non-symmetrical response is obtained since the response amplitude is limited in the closed direction. Second harmonic response components in the resonance response spectrum are then generated. If a liquid now fills the cracks, the liquid is essentially incompressible and stops the cracks from slamming shut, giving rise to a more symmetrical response, which reduces the second harmonic content of the resonance response spectrum. The second harmonic spectrum under wet and dry conditions can then be compared to detect small crack-like flaws in previously untested parts using resonant ultrasound techniques.

Figure 1:
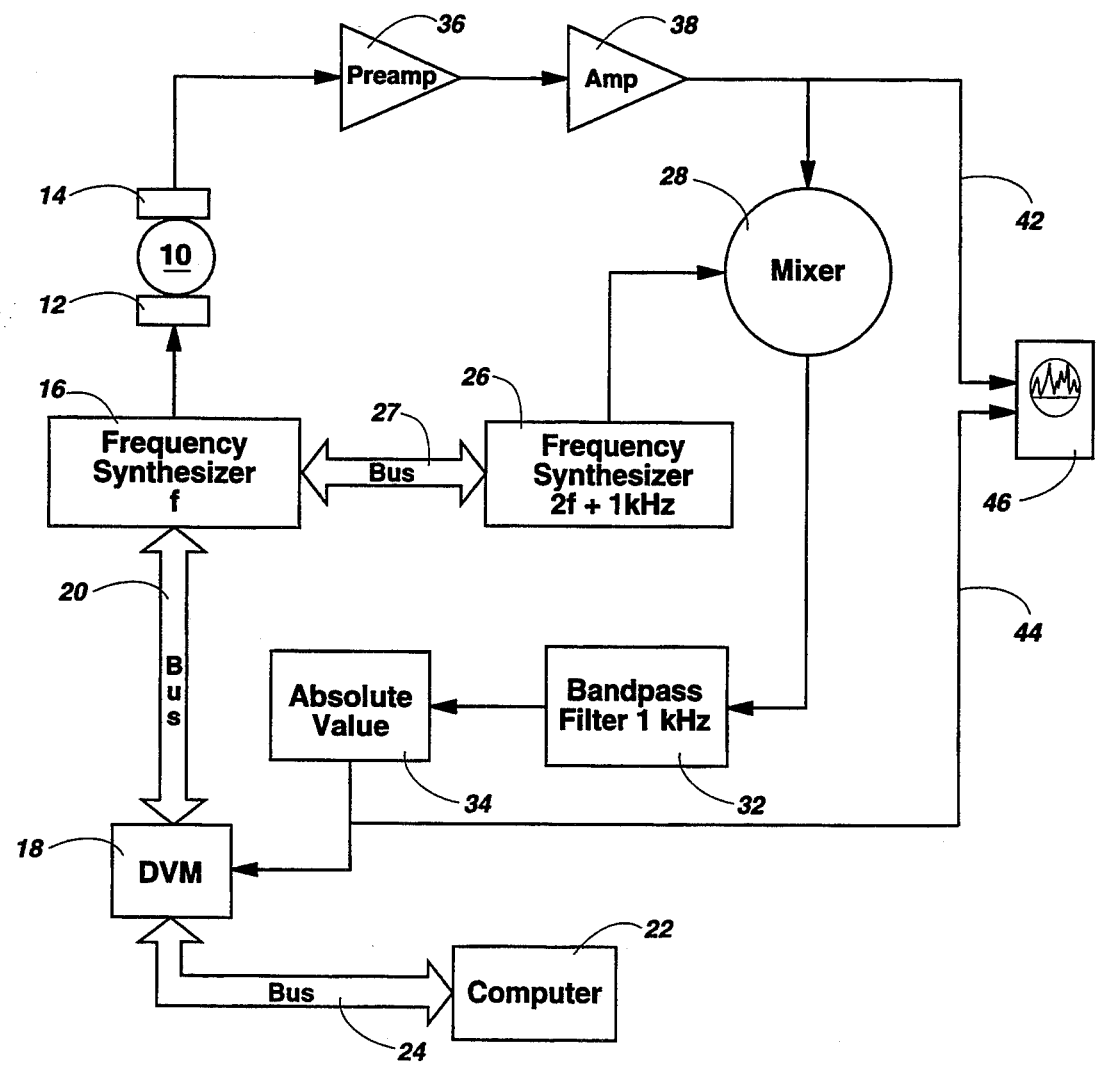
FIG. 1 is a block diagram schematic of a system for determining the second harmonic components in the frequency response of an object to an exciting frequency sweeping over a range of frequencies.

Referring first to FIG. 1, there is shown in block diagram form a schematic for an apparatus for producing a record of the second harmonic frequency components of an ultrasonic response as a function of the exciting frequency. Sample 10 is ultrasonically excited by transducer 12 and the response is detected by transducer 14. Transducers 12 and 14 may be any one of a number of types of commercially available ultrasonic transducers. The excited response 42 is output through preamplifier 36 and amplifier 38 to mixer 28 and to one channel of oscilloscope 46. The recording device may be an oscilloscope, but may be a printer or a computer memory system that subsequently allows a display or other record to be created.

Transducer 12 is excited by excitation frequency oscillator, or synthesizer, 16 that outputs a frequency, f, controlled by computer 22. Synthesizer 16 may output a plurality of individual frequencies to excite sample 10 over set a set of predetermined frequencies or may sweep the output frequency over a predetermined frequency range. The digital output commands and other data flow is along buses 20, 24, and 27, which are conventional commercial buses that comply with the standards set by industry standard IEEE 488.

Mixing frequency oscillator, or synthesizer, 26, is also controlled by computer 22 along bus 27. The output of mixing frequency synthesizer 26 is at least a frequency, 2 f, for input to mixer 28. In a preferred embodiment, the output frequency from frequency synthesizer is offset by a selected intermediate frequency (IF), e.g. 1 kHz, from the pure second harmonic frequency, 2 f. This IF offset technique is conventional and provides for noise components only in a small bandwidth to greatly improve the signal-to-noise ratio and concomitant device sensitivity.

Mixer 28 is a superheterodyne type circuit with two inputs to be heterodyned: the output response of sample 10 from amplifier 38 and the output of frequency synthesizer 26 at, e.g. 2 f+1 kHz. It can be shown that the output from heterodyning the two signals includes a component at the IF frequency, i.e., 1 kHz, having an amplitude related to the amplitude of the second harmonic frequency components in output signal 42 forming the second harmonic spectrum. The output signal from mixer 28 is input to a band pass filter 32 at the IF frequency, e.g. 1 kHz, to attenuate other frequency components. The filtered signal is input to absolute value circuit 34, whose output is a dc voltage functionally related to the amplitude of the second harmonic frequency component in the output frequencies from sample 10. The dc component from absolute value circuit 34 is input to digital voltmeter (DVM) 18, where the value may be digitized and input to computer 22 along bus 24.

The dc voltage from circuit 34 is also input to a second channel of oscilloscope 46 as a visual diagnostic. Computer 22 records input frequencies and response data to provide a record of second harmonic amplitude vs. response frequency. A comparison of the records between excitation of the dry component and the component after being wetted or otherwise coated with a liquid will clearly indicate the change in the second harmonic content of the two conditions to ascertain the existence of crack-like defects in the object.

Figure 2A:
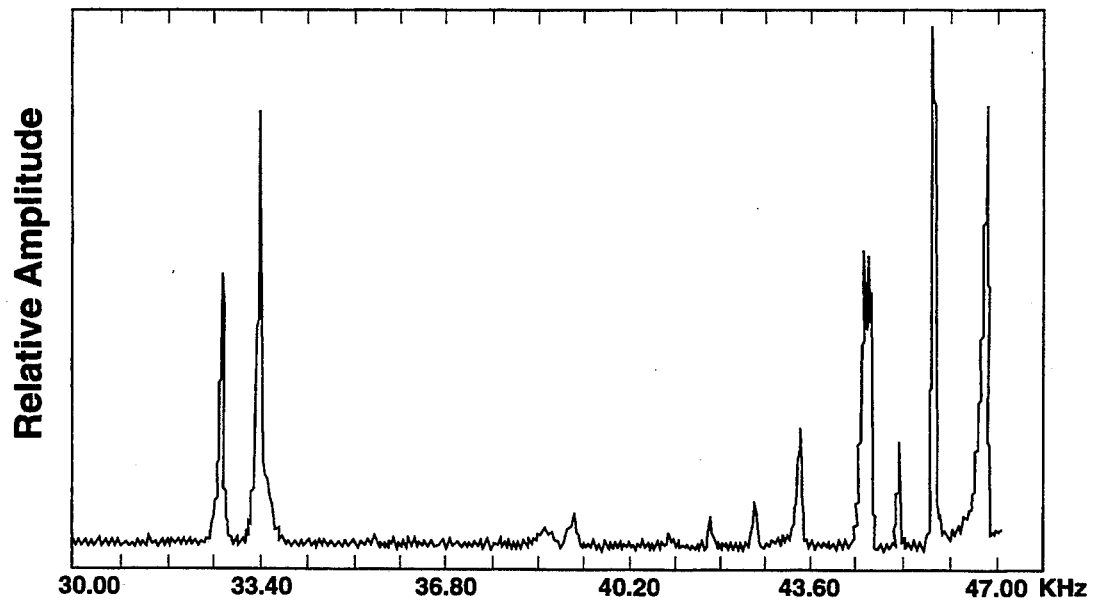
FIGS. 2A and 2B graphically depict the second harmonic components in dry and wet ultrasonic response spectra of an aluminum plate with a crack-like flaw.
Figure 2B:
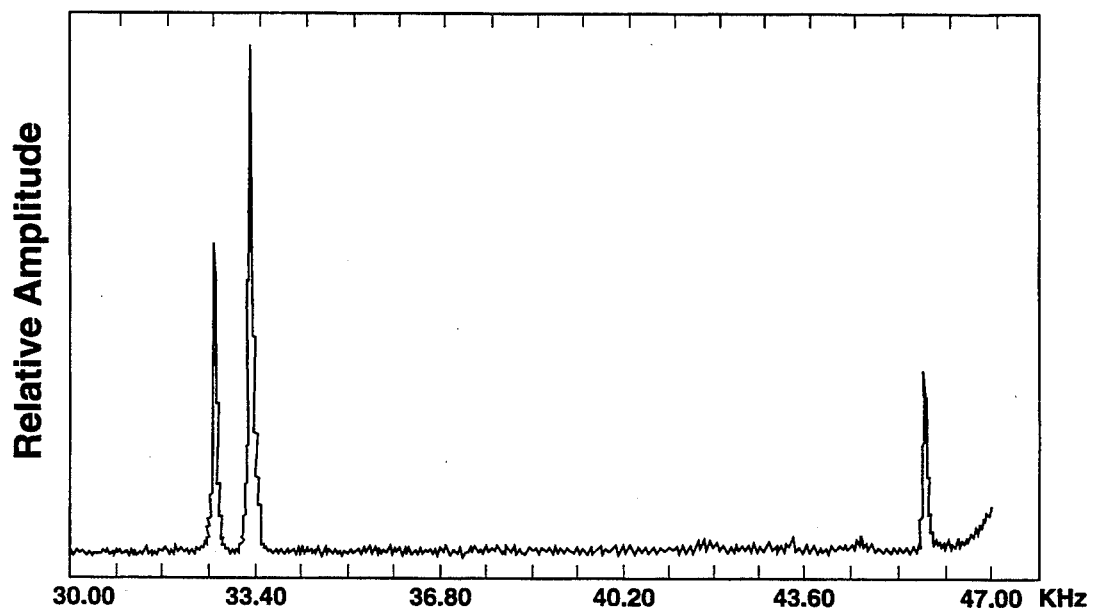

FIGS. 2A and 2B graphically depict the application of resonance ultrasound spectroscopy according to the present invention to crack detection in an electron beam welded aluminum plate. The plate was welded to simulate a microscopic crack, with the crack being continuous across almost half the plate. FIG. 2A depicts the second harmonic spectrum over a swept frequency range of 30–47 kHz. Several second harmonic peaks are readily observed. The plate was saturated with ethanol, all surface liquid was removed, and a second harmonic frequency spectrum was again generated over the same frequency range. FIG. 2B graphically shows the resulting second harmonic peaks as shown in FIG. 2A. The attenuation of the second harmonic peaks is a sensitive indication of the presence of a crack.

Figure 3A:
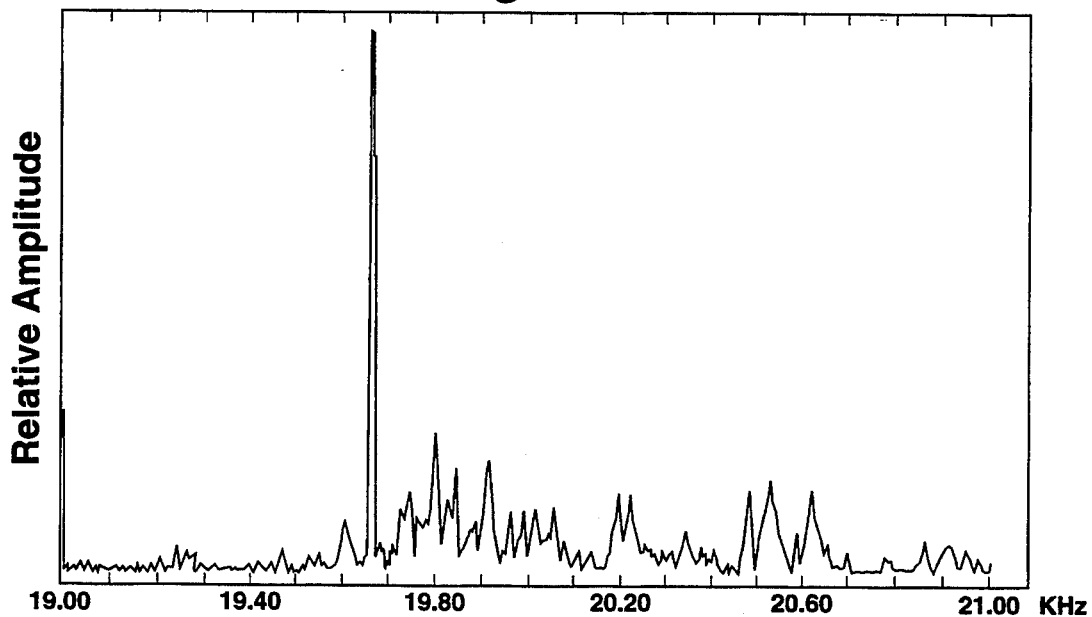
FIGS. 3A and 3B graphically depict the second harmonic components in dry and wet ultrasonic response spectra of a commercial airplane part with a crack-like flaw.
Figure 3B:
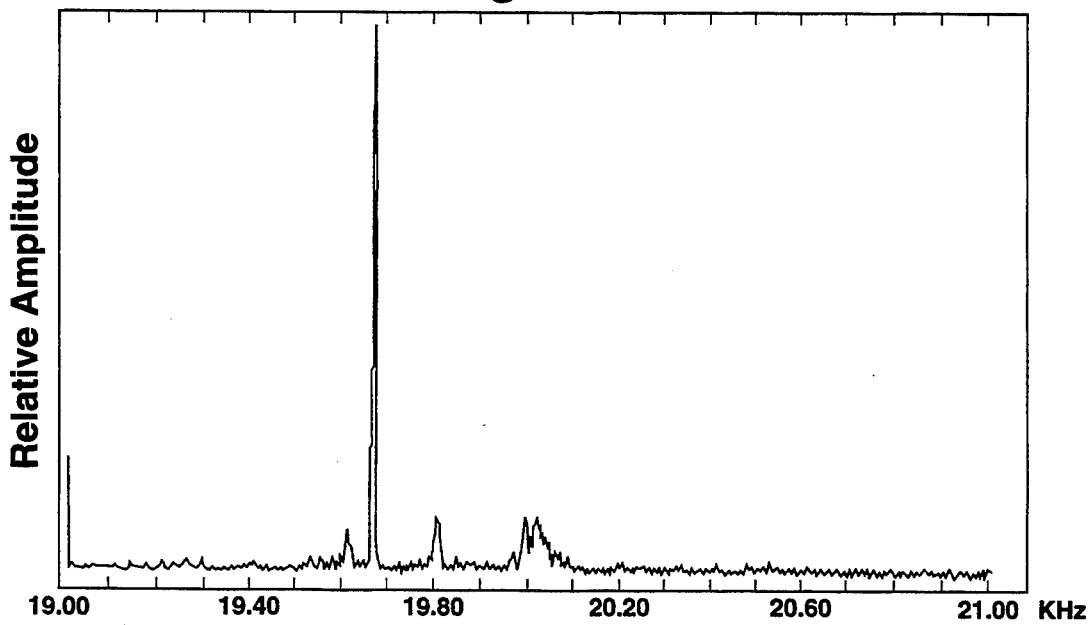

FIGS. 3A and 3B graphically depict the ultrasound inspection results of an airplane wheel. FIG. 3A is the second harmonic spectrum of the "dry" wheel and FIG. 3B is the second harmonic spectrum of the "wet" wheel. The attentuation of second harmonic frequencies is readily apparent. The wheel was known to have at least one crack one-half inch long.

It is apparent from FIGS. 2A, 2B, 3A, and 3B that the second harmonic spectrum obtained according to the present invention allows the ready detection of crack-like flaws in components without the need for any reference spectrum other than the spectrum obtained with the part in a "dry" condition. The attentuation of second harmonic components in a flawed component after coating with a suitable liquid can be visually observed, e.g., on a oscilloscope or a plotted graph, or can be automatically detected, e.g., using a suitable software routine in a computer to locate and compare peaks in the second harmonic spectrum.

The method of the present invention can be applied with any technique that alters the asymmetry of the crack response to acoustic energy. For example, the second harmonic of the acoustic resonance response could be obtained under different temperature conditions. The expanded size of the crack at higher temperatures would provide a more symmetric response, i.e., attenuated second harmonic components. Likewise, the components might be placed under a strain to open the crack and prevent crack closing to attenuate at least some frequencies in the second harmonic response when a crack is present.

The foregoing description of the invention has been presented for purposes of illustration and description. It is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed:

1. A method for detecting crack-like flaws in a work piece comprising the steps of:
    establishing said work piece in a first condition to produce a first response of said crack-like flaws to an acoustic excitation;
    acoustically exciting said work piece over a selected range of resonant ultrasound frequencies to generate a first spectrum containing second harmonic components in said first response of said component;
    establishing said work piece in a second condition to produce a second response of said crack-like flaws to said acoustic excitation;
    acoustically exciting said work piece over said selected range of resonant ultrasound frequencies to generate a second spectrum containing second harmonic components in said second response of said work piece; and
    comparing said first and second spectra to determine the presence of said crack-like flaws.

2. A method according to claim 1, wherein the step of generating said second harmonic components includes the steps of:
    generating a second plurality of frequencies at a frequency of at least the second harmonic frequencies of said selected range of resonant ultrasound frequencies; and
    mixing said second plurality of frequencies with corresponding frequencies in said first and second responses of said component to output spectra corresponding to said second harmonic components in said first and second responses of said component.

3. A method according to claim 2, further including the step of generating each frequency in said second plurality of frequencies at a selected IF frequency offset from said second harmonic of each corresponding exciting frequency, wherein mixing said second plurality of frequencies with said first or second ultrasonic resonance spectrum generates an output at said selected IF frequency having amplitudes functionally related to said second harmonic components in said first or second resonance spectrum.

4. A method for detecting crack-like flaws in a work piece comprising the steps of:
    generating from a plurality of exciting frequencies a first ultrasonic resonance spectrum of said work piece in a dry condition;
    wetting said work piece with a selected liquid to penetrate any crack-like flaws in said work piece;
    generating from said plurality of exciting frequencies a second ultrasonic resonance spectrum of said work piece after said wetting; and
    determining second harmonic components in said first and second ultrasonic resonance spectra related to each one of said plurality of exciting frequencies to ascertain the presence of said crack-like flaws in said work piece.

5. A method according to claim 4, wherein the step of determining said second harmonic components includes the steps of:
    generating a second plurality of frequencies at a frequency of at least the second harmonic frequencies of said exciting frequencies; and
    mixing said second plurality of frequencies with corresponding frequencies in said first and second ultrasonic resonance spectra to output spectra corresponding to said second harmonic components in said first and second ultrasonic resonance spectra.

6. A method according to claim 5, further including the step of generating each frequency in said second plurality of frequencies at a selected step frequency offset from said second harmonic frequency of each corresponding exciting frequency, wherein mixing said second plurality of frequencies with frequencies forming a resonance response spectrum generates an output at said selected step frequency having amplitudes functionally related to said second harmonic components in said resonance response spectrum.

7. Apparatus for generating an ultrasonic resonance spectrum of a work piece indicative of crack-like flaws arising from manufacture or use of said work piece, comprising:
    means for generating from a plurality of exciting frequencies first and second ultrasonic resonance spectra of a work piece;
    means for generating second harmonic spectra from frequency components in said first and second ultrasonic resonance spectra related to each one of said plurality of exciting frequencies; means for placing said work piece in at least two conditions that affect a response of said crack-like flaws to said plurality of exciting frequencies; and
    means for comparing said second harmonic spectra of said first and second ultrasonic resonance spectra from said work piece in each of said at least two conditions to determine the presence of crack-like flaws in said work piece.

8. Apparatus according to claim 7, wherein said means for generating second harmonic spectra further comprises:

oscillator means for generating a plurality of mixing frequencies with each mixing frequency being at least the second harmonic frequency of each corresponding frequency in said plurality of exciting frequencies; and mixer means to heterodyne said mixing frequencies with said first and second ultrasonic resonance spectra to output a signal indicative of second harmonic components in said first and second ultrasonic resonance spectra.

9. Apparatus according to claim 7, wherein said means for generating said second harmonic spectra further comprises:

oscillator means for generating a plurality of mixing frequencies with each mixing frequency being offset by a selected step frequency from the second harmonic frequency of each exciting frequency;

mixer means to heterodyne said mixing frequencies with said first and second ultrasonic resonance spectra to output a signal containing a frequency component at said selected step frequency; and means for detecting the amplitude of said selected step frequency output from said mixer means for each said mixing frequency, wherein said amplitude is functionally related to a second harmonic component of said first and second ultrasonic resonance spectra at each said exciting frequency.

10. Apparatus for detecting crack-like flaws in a work piece using an ultrasonic resonance spectrum, comprising:

first transducer means for ultrasonically exciting said work piece at a first selected ultrasonic frequency;

second transducer means for detecting the ultrasonic response of said work piece to said first selected ultrasonic frequency;

oscillator means for generating a second harmonic frequency of said selected ultrasonic frequency;

mixer means for heterodyning said ultrasonic response of said work piece and said second harmonic frequency to generate an output functionally related to an amplitude of a second harmonic of said selected ultrasonic frequency in said ultrasonic response;

means for sweeping said selected ultrasonic frequency over a predetermined frequency range; and means for recording and analyzing said output from said mixer means as said selected ultrasonic frequency is swept over said predetermined frequency range, wherein said output is representative of the presence of a crack-like flaw in said work piece.

* * * * *